(12) United States Patent
Zarembo (10) Patent No.: US 7,240,833 B2
(45) Date of Patent: Jul. 10, 2007

(54) SYSTEM AND METHOD OF MANAGING INFORMATION FOR AN IMPLANTABLE MEDICAL DEVICE

(75) Inventor: Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 44 days.

(21) Appl. No.: 10/850,156

(22) Filed: May 20, 2004

(65) Prior Publication Data

US 2005/0258242 A1 Nov. 24, 2005

(51) Int. Cl.
*G06F 19/00* (2006.01)
*G06Q 30/00* (2006.01)
*G06Q 90/00* (2006.01)

(52) U.S. Cl. .................. 235/385; 607/30; 235/487

(58) Field of Classification Search ................ 235/385, 235/438, 485–487; 607/1, 30–32, 57–65; 713/182, 193
See application file for complete search history.

(56) References Cited

U.S. PATENT DOCUMENTS

| | | | |
|---|---|---|---|
| 5,423,334 A | 6/1995 | Jordan | 128/899 |
| 5,549,646 A * | 8/1996 | Katz et al. | 607/8 |
| 5,724,985 A * | 3/1998 | Snell et al. | 600/510 |
| 5,749,907 A * | 5/1998 | Mann | 607/27 |
| 5,843,139 A * | 12/1998 | Goedeke et al. | 607/32 |
| 5,908,392 A * | 6/1999 | Wilson et al. | 600/509 |
| 5,911,738 A * | 6/1999 | Sikorski et al. | 607/19 |
| 6,150,934 A | 11/2000 | Stiglic | 340/505 |
| 6,167,310 A * | 12/2000 | Grevious | 607/32 |
| 6,292,697 B1 * | 9/2001 | Roberts | 607/27 |
| 6,327,501 B1 * | 12/2001 | Levine et al. | 607/27 |
| 6,361,522 B1 * | 3/2002 | Scheiner et al. | 604/67 |
| 6,385,593 B2 * | 5/2002 | Linberg | 705/28 |
| 6,442,432 B2 * | 8/2002 | Lee | 607/59 |
| 6,508,400 B1 * | 1/2003 | Ishifuji et al. | 235/382 |
| 6,615,074 B2 | 9/2003 | Mickle et al. | 600/509 |
| 6,766,200 B2 * | 7/2004 | Cox | 607/60 |
| 7,039,810 B1 * | 5/2006 | Nichols | 713/182 |
| 2003/0018369 A1 | 1/2003 | Thompson | 607/60 |
| 2003/0209601 A1 * | 11/2003 | Chung | 235/385 |
| 2005/0070975 A1 * | 3/2005 | Zeijlemaker et al. | 607/60 |
| 2005/0107839 A1 * | 5/2005 | Sanders | 607/32 |
| 2005/0241026 A1 * | 10/2005 | Esler et al. | D24/100 |
| 2006/0074463 A1 * | 4/2006 | Seeberger et al. | 607/60 |
| 2006/0173259 A1 * | 8/2006 | Flaherty et al. | 600/331 |

OTHER PUBLICATIONS

"EM Microelectronic's Product List Relating to RFID ICs", http://www.emmicroelectronic.com/Line.asp?IdLine=3, (observed Sep. 22, 2004), 2 Pages.

Jacomet, M., et al., "Contactless Identification Device With Anti-collision Algorithm", *IEEE Computer Society, CSCC'99, Conference on Circuits, Systems Computers and Communications, Jul. 4-8, 1999*, (http://www.microlab.ch/industry/r_and _d/research/cscc/cscc99.pdf), 6 Pages.

* cited by examiner

*Primary Examiner*—Thien M. Le
*Assistant Examiner*—Edwyn Labaze
(74) *Attorney, Agent, or Firm*—Schwegman, Lundberg, Woessner & Kluth (57) ABSTRACT

A method of collecting information related to manufacture of an implantable medical device, storing the information in a radio frequency identifier (RFID) unit, updating the information stored in the RFID unit during manufacturing of the implantable medical device, and transferring the information from the RFID unit to other devices.

37 Claims, 5 Drawing Sheets

SYSTEM AND METHOD OF MANAGING INFORMATION FOR AN IMPLANTABLE MEDICAL DEVICE

TECHNICAL FIELD

The field generally relates to implantable medical devices and, in particular, but not by way of limitation, to a system and method for managing information related to implantable medical devices using a radio frequency identifier (RFID) unit.

BACKGROUND

Implantable medical devices (IMDs) are devices designed to be implanted into a patient. Some examples of these devices include cardiac rhythm management (CRM) devices such as implantable pacemakers and implantable cardioverter defibrillators (ICDs). The devices are used to treat patients using electrical therapy and to aid a physician or caregiver in patient diagnosis through internal monitoring of a patient's condition. Implantable devices may also include electrical leads that are either separate from, or connected to, a CRM. Electrical leads connected to a CRM are in communication with sense amplifiers of the CRM devices to monitor electrical heart activity within a patient. The CRM devices often include sensors to monitor other internal patient parameters. Other examples of implantable medical devices include implantable insulin pumps or devices implanted to administer drugs to a patient. Because the devices are implantable and often complex, manufacturing of IMDs requires management of a large quantity of information. This information often needs to track the device through the duration of its manufacture to the implant procedure and sometimes throughout the life of the device. It is desirable to streamline the management of the information and maintain information integrity.

SUMMARY

Systems and methods are provided for managing information related to implantable medical devices. In one system example, the system comprises an implantable medical device and at least one RFID unit external to the implantable medical device, where the RFID unit is to be packaged with the implantable medical device. The RFID unit is operable to contain stored information that includes information related to manufacturing of the implantable medical device.

One method example comprises reading information related to manufacture of an implantable medical device, storing the assembly information in the RFID unit, and updating the assembly information stored in the RFID unit during manufacturing of the implantable medical device. Other examples and advantages are also discussed in the following detailed description and represented in the drawings that form a part thereof.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

Systems and methods for managing information related to implantable medical devices (IMDs) are discussed herein. The information may include, but is not limited to, manufacturing information such as inventory information, assembly management information, measurement results, IMD specifications, traceability information and also information related to a procedure implanting the device.

The IMDs may include, without limitation, a pacer, a defibrillator, a cardiac resynchronization therapy (CRT) device, a combination of such devices, electrical leads coupled with such devices to deliver electrical therapy, and also guide wires and guide catheters used to in implanting the electrical leads. The IMDs may also include devices that are purely diagnostic in nature such as devices implanted to communicate diagnostic data to an external device, and also to IMDs that deliver a drug therapy to a patient. The IMDs may further include vascular intervention devices such as stents and balloon angioplasty devices.

Figure 1:
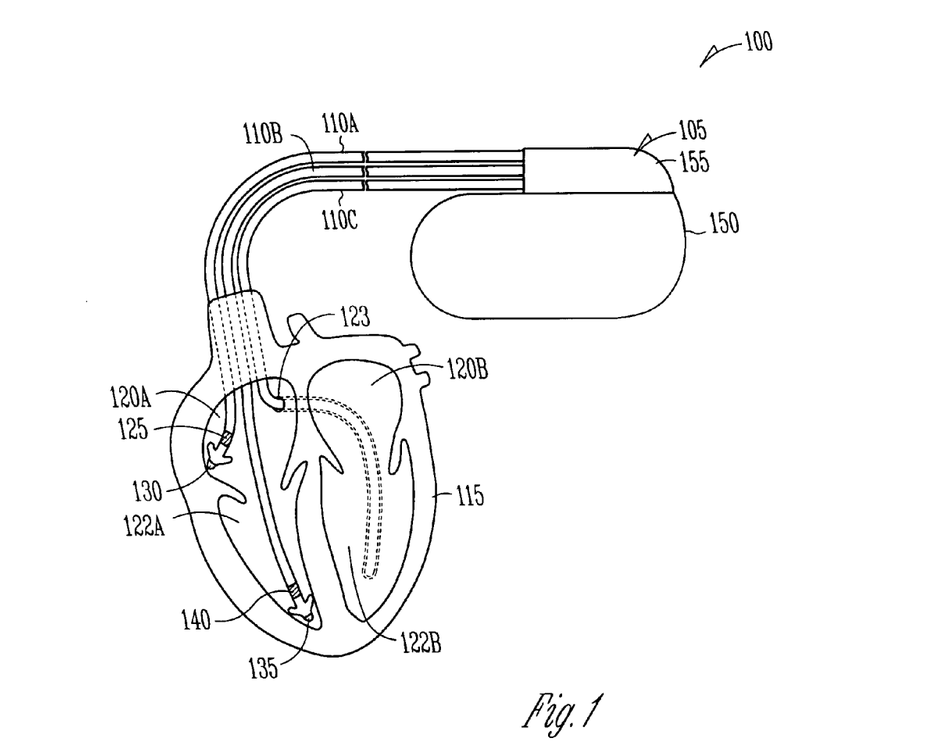
FIG. 1 illustrates implantable medical devices (IMDs), including a pulse generator and implantable electrical leads, coupled to a heart.

FIG. 1 illustrates a system 100 using IMDs that include a pulse generator (PG) 105 and one or more leads 110A, B, C to couple the PG 105 to the heart 115. Heart 115 includes a right atrium 120A, a left atrium 120B, a right ventricle 122A, a left ventricle 122B, and a coronary sinus 123 extending from right atrium 120A. In one embodiment, atrial lead 110A includes electrodes (electrical contacts, such as ring electrode 125 and tip electrode 130) disposed in, around, or near an atrium 120 of heart 115 for sensing signals and/or delivering pacing therapy to the atrium 120. Ventricular lead 110B includes electrodes (electrical contacts, such as ring electrode 140 and tip electrode 135) disposed in, around, or near a right ventricle 122A of heart 115 for sensing signals and/or delivering pacing therapy to the ventricle 122A. Coronary venous lead 110C includes electrodes disposed in, around, or near a left ventricle 122B. Leads 110A–C optionally also include additional electrodes, such as for delivering atrial and/or ventricular cardioversion/ defibrillation and/or pacing or resynchronization therapy to the heart 115. PG 105 includes components that are enclosed in a hermetically-sealed canister or "can" 150. Additional electrodes may be located on the can 150, or on an insulating header 155, or on other portions of PG 105, for providing unipolar pacing and/or defibrillation energy in conjunction with the electrodes disposed on or around heart 115.

IMDs are often comprised of complex assemblies and subassemblies. Because of the medical applications of IMDs, a large quantity of information often needs to be cross-referenced to the IMD through the manufacturing process. This includes, but is not limited to information related to components used in the assemblies, information related to the assembly process, and any traceability information. This information is related to the assemblies through serial numbers, model numbers, device specifications and the like. Also, some of this information is useful at the time of implant of the device. While some IMDs are often capable of communication with external devices or programmers, other IMDs and devices used in an implant procedure are not. It would be desirable to cross reference the information in a convenient form, thereby making it easier for manufacturers, hospitals and clinicians to handle the information and for the information to follow the IMDs throughout the manufacturing process, through inventory control, and to the implant procedure.

Figure 2:
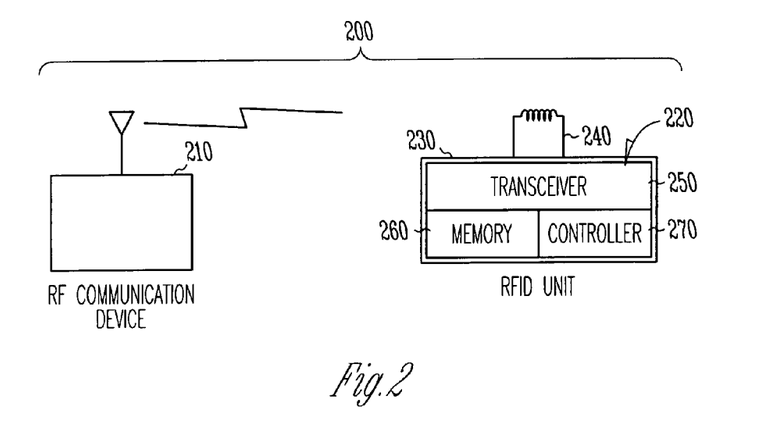
FIG. 2 is a block diagram illustrating embodiments of a radio frequency (RF) communication device and a radio frequency identifier (RFID) unit.

Radio frequency identifier (RFID) units are devices designed to communicate with an RF communication device over frequencies that range from hundreds of kilohertz (kHz) to hundreds of megahertz (MHz). They are designed inexpensively so that they may be used as disposable tags that provide information when interrogated. Using RFID units during manufacture of the IMDs will provide the aforementioned information in a convenient and reliable form. FIG. 2 is a block diagram 200 illustrating embodiments of a radio frequency (RF) communication device 210 and a radio frequency identifier RFID unit 220. The RFIDs 220 include, for example, semiconductor circuits 230 and antennas 240. The semiconductor circuits 230 include transceiver circuits 250 for communication and memory circuits 260 such as ROM, EEPROM or static RAM for storage. The RFIDs 220 typically include an amount of memory 260 ranging from sixty-four bits to two thousand bits. As memory density continues to increase due to advancing technology, more memory will be available on an RFID unit 220 for information storage. The RFID units 220 may contain read/write or read only memory 260. The semiconductor circuits 230 also include a controller circuit 270 that is operable to control accesses to the memory 260 and to receive and transmit information using the transceiver circuit 250.

The RFID units 220 include active devices that require battery power as well as passive devices that receive their activation power through the energy transferred in RF communications. Such passive devices include a power circuit to transform the energy transferred into a power source for the RFID unit. Because the passive devices don't include a battery, they can be contained in extremely small packages such as, for example, a 10 millimeter (mm) by 2 mm package. Typically the package for the RFIDs 220 includes inert materials such as, for example, a glass encapsulation.

The RF communication device 210 is used to interrogate and/or write to the RFID units 220. In one embodiment, the RF communication device is the same as, or a part of, the IMD programmer used during implant procedures. In another embodiment, the RF communication device is a separate unit from the IMD programmer. In yet another embodiment, the RF communication device 210 is in communication with a global or hospital computer network. For example, an RF communication device communicates with a programmer or network via a USB port, SCSI port, Firewire port, or any other communication port associated with the programmer or computer on the network. The access to a computer network makes the information read from an RFID unit 220 available over the network and allows the RF communication device 220 to acquire information over the network for storage in the RFID unit 210. For example, information read from an RFID unit 220 can be compared to information on the network that is related to a product recall.

Figure 3:
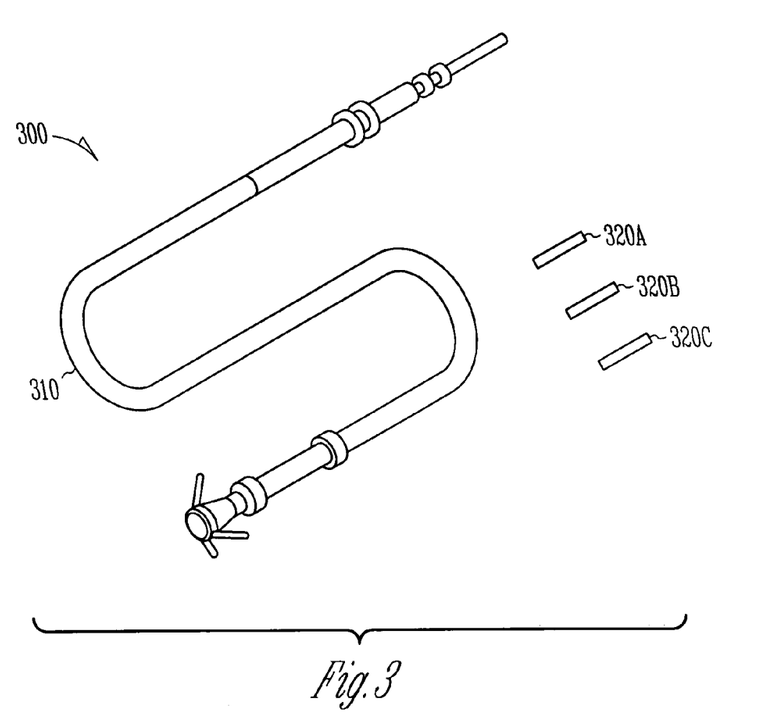
FIG. 3 illustrates an exemplary embodiment of a system comprising an IMD associated with at least one RFID unit.

FIG. 3 illustrates an exemplary embodiment of a system 300 comprising an IMD associated with at least one RFID unit 320A. The IMD shown is a final assembly for an implantable electrical lead 310.

The RFID unit 320A contains information related to manufacture of the lead 310. In one embodiment, the information includes a unique identifier for the assembly, such as a serial number, model number, or the like. In other embodiments, the information includes assembly length, diameter, device specifications, material composition, or compatibility of the device with a magnetic resonance imaging (MRI) procedure. In yet another embodiment, the information includes traceability information such as a date that an event related to manufacturing occurred. For example, the event may be beginning a task, completing a test or taking a measurement. In yet another embodiment, the information includes an identifier for a component or a subassembly and/or a date that the component or subassembly was added to the final assembly. To enter component data into an RFID unit 320A–C, an assembler or other worker at a workstation enters the component information into a computer. The assembler can enter this information by hand or by using an automated method such as a bar code reader or by downloading a file. The computer is in communication with an RF communication device to enter the component information into the RFID unit 320A–C.

In yet another embodiment, the RIFD unit 320A–C includes test or measurement information such as lead impedance information for the final assembly. In an example of the embodiment, the impedance information includes a resistance measurement. In another example, the impedance information includes an inductance measurement. In yet another embodiment, the RFID unit 320A–C includes shelf life information for one or more of the components therein.

The system 300 may include one or a plurality of RFID units 320A–C. In one embodiment, a first RFID 320A is associated with the lead 310. In another embodiment, a first RFID 320A and a second RFID 320B are associated with the lead 310. In the embodiment, the first RFID 320A is designed to transfer data to a communication device over short distances, such as up to one foot. A short programming distance is useful, for example, to transfer data during assembly while working at a workstation in an area with multiple workstations. The short programming distance prevents interference between workstations. The second RFID 320B is designed to transfer data over longer distances, such as up to fifteen feet. A longer programming distance is useful, for example, to interrogate an inventory area to quickly determine if an assembly associated with the RFID 320 is in the area. In yet another embodiment, a third RFID 320C is associated with the lead 310 to transfer data over medium distances, such as up to three feet. A medium programming distance is useful, for example, to interrogate a workstation to determine if an assembly is present at the workstation in an area containing multiple workstations. Since the communication distance of the individual RFIDs 320A–C may be related to a use of the RIFD, each of the plurality of RFID units 320A–C may contain the same information as another RFID or each RFID may contain unique information associated with the IMD.

Figure 4:
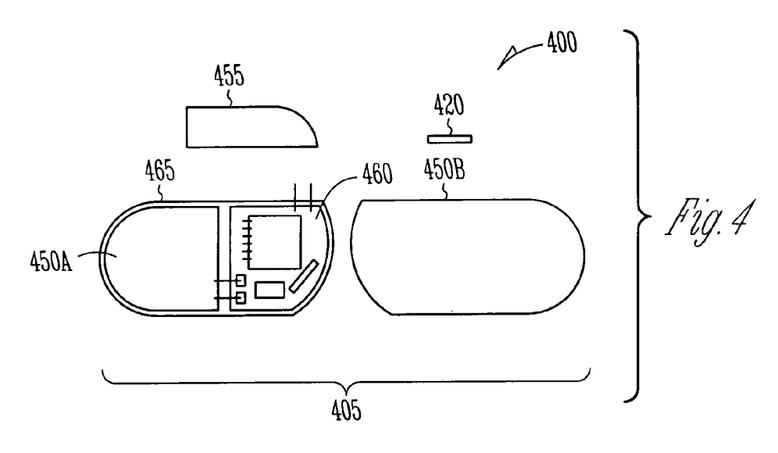
FIG. 4 illustrates another exemplary embodiment of a system comprising an IMD associated with at least one RFID unit.

FIG. 4 illustrates another exemplary embodiment of a system 400 comprising an IMD associated with at least one RFID unit 420. The IMD shown is an implantable pulse generator 405. The IMD is shown before can halves 450A, B are coupled together and the header subassembly 455 is attached to complete the final assembly. Also shown are a hybrid circuit subassembly 460 and a battery 465. In one embodiment, the at least one RFID unit 420 includes information related to the subassemblies 455, 460. One of ordinary skill in the art will understand upon reading this detailed description that associating RFID units 420 with additional subassemblies not shown herein is within contemplation of the present application. In another embodiment, the at least one RFID 420 includes an RFID unit for each subassembly and the final assembly. In yet another embodiment, at least some information is read from the RFID units 420 for the subassemblies and stored into the RFID unit 420 for the final assembly. This storing of information would generally be done as the final assembly is completed or nears completion. In one embodiment this information includes reading and storing unique identifiers for the subassemblies such as serial and model numbers. In other embodiments, the RIFD units 420 include test or measurement information. Further embodiments include information related to the battery 465 such as expected battery life at specified IMD settings, and information related to the hybrid circuit subassembly 460 such as a unique identifier, measurement information or test information.

Returning to the RFID unit in FIG. 2, if an assembly area includes multiple workstations for assembling IMDs, the assembly area may contain several RFID units 220 able to communicate with an RF communication device 210. If several RFID units 220 are within the communication range of the RF communication device 210, the possibility exists that multiple RFID units 220 will respond to the RF communication device 210 at the same time. Thus, in one embodiment, the RFID units 220 and RF communication device 210 incorporate anti-collision technology in their communications. Anti-collision technology generally detects collisions and resolves the collisions by having the RFID units 220 that are within range of the RF communication device 210 transmit in a certain order, for example, serially. Use of this technology allows for reading information from a plurality of RFID units 220 belonging to one assembly, and verifying that the plurality of RFID units 220 belong to a same assembly.

Yet another embodiment includes packaging an RFID unit 220 with an IMD final assembly. One advantage of packaging the RFID unit 220 with the IMD is that it assists in inventory control of final packaged product. For example, determining that a specific IMD is within a controlled inventory area is accomplished by transmitting the serial number of the IMD and obtaining a response from the packaged RFID unit 220. Another advantage is that it allows for configuration of programmable IMDs using information read from RFID units 220 before an implant procedure begins. For example, a programmable IMD such as a pulse generator can be configured with lead information before the packages are opened. An RF communication device 210 reads lead information such as a serial number, model number or lead impedance from an RFID unit 220 and writes the information into the programmable IMD. The information in the RFID unit may also indicate compatibility among the IMDs being implanted. For example, the RFID unit may indicate that an electrical lead is not compatible with a pulse generator.

Figure 5:
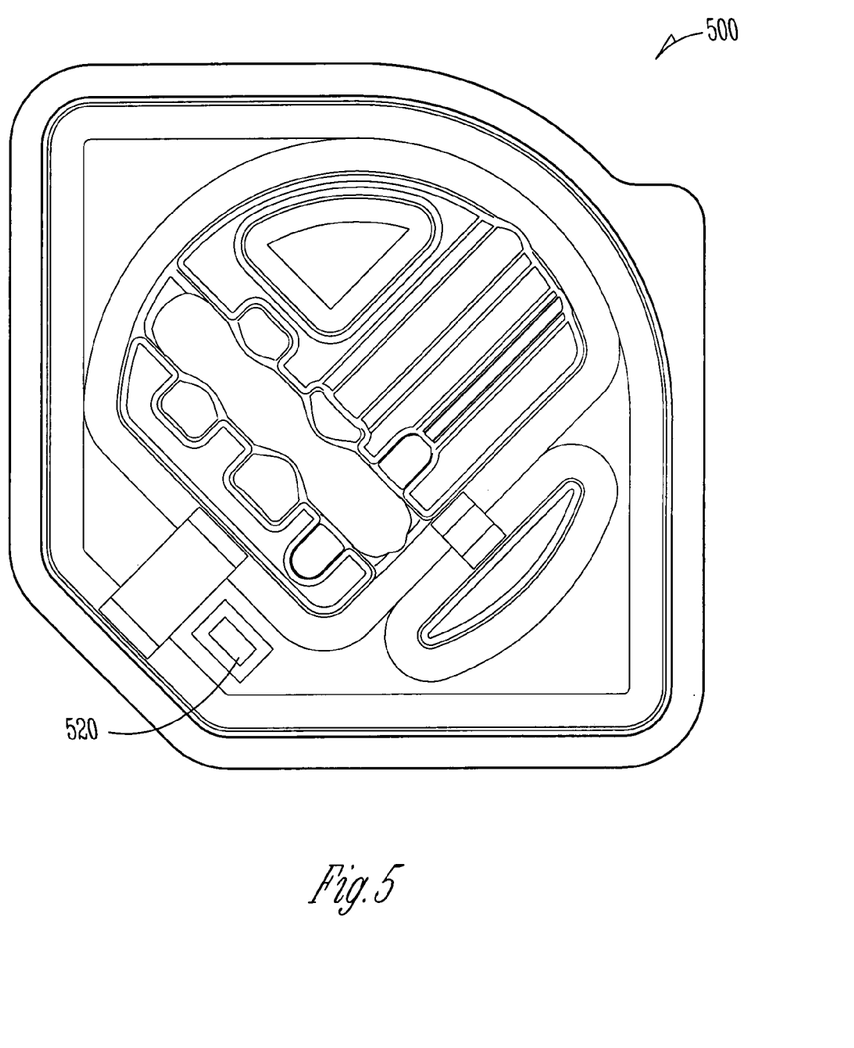
FIG. 5 is an illustration of an embodiment of an inner tray used to package an IMD and an RFID unit within a hermetically sealed package.

A further embodiment includes packaging the RFID unit within a hermetic sterile package of an IMD. FIG. 5 is an illustration of an embodiment 500 of an inner tray used to package an MD and an RFID unit 520 within a hermetically sealed package. Packaging within the sterile package allows the RFID unit 520 to enter the sterile field during a procedure an implant procedure and makes the information contained in the RFID 520 readily available. By having the RFID unit 520 within the sterile field, information concerning the implant procedure can also be stored into the RFID unit 520 while the procedure is taking place. In one embodiment, information is read and stored into the RFID unit 520 using the same programmer used to program a programmable IMD. In another embodiment, information is read from an RFID unit 520 and written into a programmable IMD which alters its settings based on the written information. For example, the IMD may limit its voltage output range in response to a lead model number obtained from the RFID unit 520. In another example, an initial lead impedance value read from the RFID unit 520 is stored into the IMD. The IMD monitors the lead impedance and detects if the lead impedance varies to such a substantial degree from the initial value that the IMD is able to determine that a problem with the lead has developed since the implant procedure. In yet another embodiment, the lead information is read from a first RFID unit 520 packaged with the lead and is programmed into the programmable IMD and a second RFID unit 520 packaged with the IMD. The MD may alter settings related to pacing modes or pacing vectors based on the information. In yet another embodiment, the RFID unit contains information concerning guide wires and/or guide catheters used during an implant procedure.

Other examples of storing information in the RFID unit 520 include storing information related to the implant procedure such as patient information, physician information, hospital information, date or time of the implant procedure, and the like, or combinations of such information.

By having the RFID unit 520 available separately from the IMD, the RFID unit 520 and the information stored is available for return to the manufacturer after the implant procedure but before explanting of the IMD. Also, information concerning the procedure is easily read from the RFID unit 520 or units after an implant procedure and entered into hospital computers.

Figure 6:
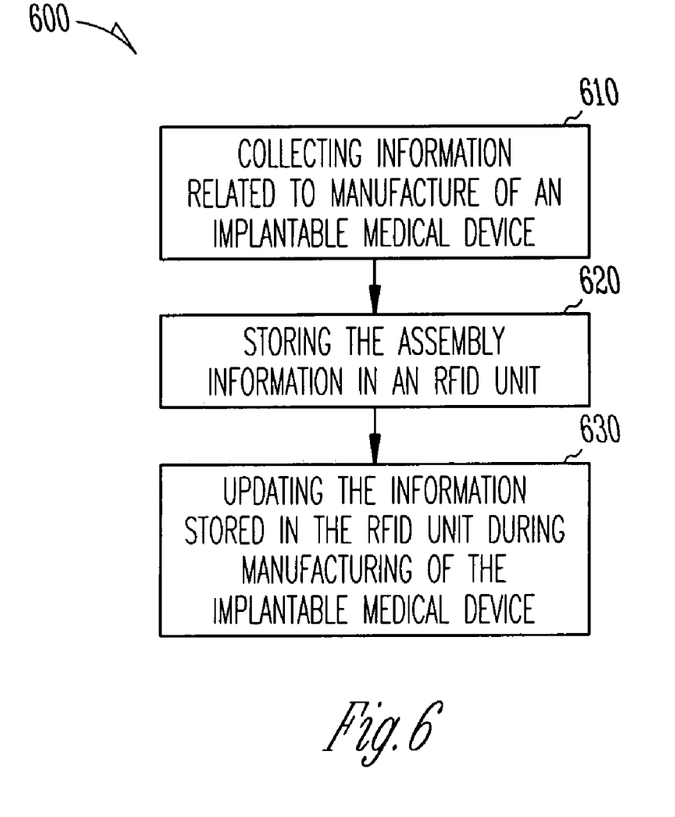
FIG. 6 shows an embodiment of a method of managing information related to an IMD using an RFID unit.

FIG. 6 shows an embodiment of a method 600 of managing information related to an IMD using an RFID unit. At 610, information associated with the manufacture of an implantable medical device is collected. Collecting information encompasses simply reading of information by a worker, or obtaining the information by an automated process such as file downloading or an optical method such as bar code reading. At 620, the information is stored in the RFID unit using an RF communication device. In one embodiment, the RF communication device is controlled by a computer. In another embodiment, the RF communication device is a programmer for an IMD. In yet another embodiment, the RF communication device is a wireless communication device. At 630, the information stored in the RFID unit is read and updated during manufacturing of the implantable medical device using an RF communication device.

Figure 7:
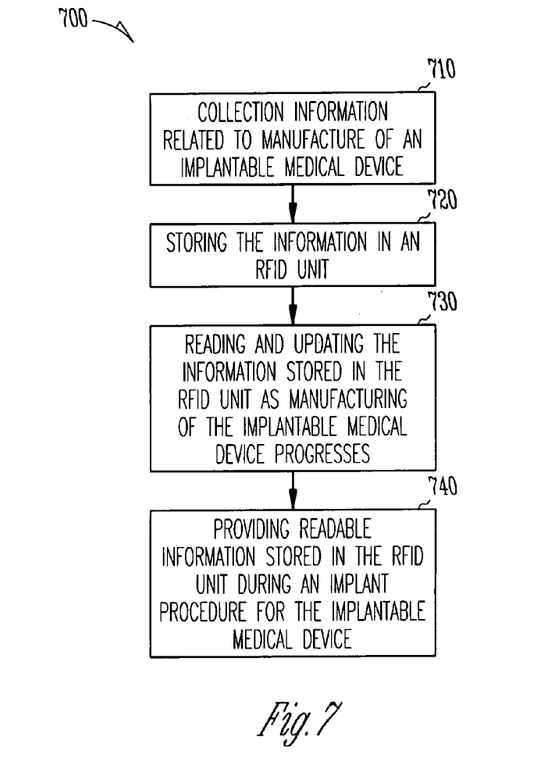
FIG. 7 shows another embodiment of a method of managing information related to an IMD using an RFID unit.

FIG. 7 shows another embodiment of a method 700 of managing information related to an IMD using an RFID unit. At 710, information related to manufacturing of an MD is collected. At 720, the information is stored in the RFID unit. At 730, information stored in the RFID unit is read and updated as manufacturing of the IMD progresses. The information may include information that is specific to the IMD. The reading and updating is accomplished by any of the means described previously herein. At 740, readable information is provided during an implant procedure for the IMD. In another embodiment, providing readable information includes providing information that can then be stored into the IMD during an implant procedure and the IMD is operable to alter its settings based on the stored information. In yet another embodiment, the readable information is used to configure the IMD. In yet another embodiment, storage is provided for entering information concerning the implant procedure into the RFID unit. In another embodiment, the implant procedure information is readable by the manufacturer when the RFID unit is returned to the manufacturer after the implant procedure.

Figure 8:
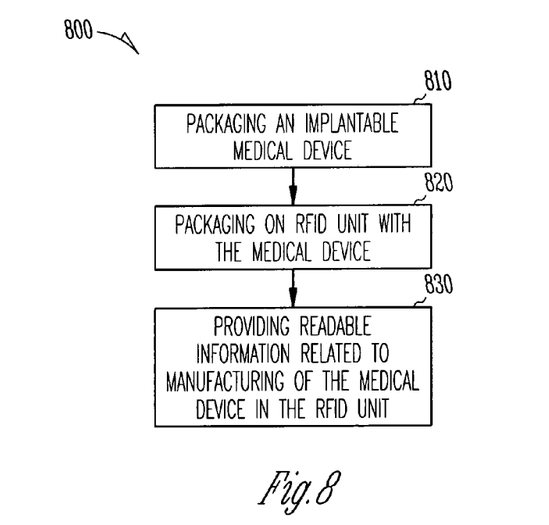
FIG. 8 shows yet another embodiment of a method of managing information related to an IMD using an RFID unit.

FIG. 8 shows yet another embodiment of a method 800 of managing information related to an IMD using an RFID unit. At 810, an implantable medical device is packaged. At 820, an RFID unit is packaged with the medical device. In one embodiment, packaging includes placing the RFID unit into the same package as the IMD. In another embodiment, packaging of the device includes packaging within a sterile inner package. In another embodiment, packaging includes incorporating the RFID into the package itself. For example, the RFID unit may be added to a label on or within the package. At 830, readable information related to manufacturing of the medical device is provided in the RFID unit. In another embodiment, the readable information includes IMD compatibility information. In yet other embodiments, the method includes providing for storage of patient, clinic and physician data into the RFID unit. In a further embodiment, the method includes providing for storage of information related to an implant procedure.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A method comprising:
   collecting information related to manufacture of a first device, wherein the first device is an implantable medical device;
   storing the information in a second device, wherein the second device includes an RF communication device;
   storing the information in a third device using the second device, wherein the third device is a passive radio frequency identifier (RFID) unit; and
   updating the information stored in the passive RFID unit during manufacturing of the implantable medical device.

2. The method of claim 1, wherein storing the information in the RFID unit includes storing a unique identifier for a manufacturing assembly in the RFID unit.

3. The method of claim 1, wherein storing the information in the RFID unit includes storing a beginning assembly date.

4. The method of claim 1, wherein updating the information in the RFID unit includes storing test results for the components in the RFID unit.

5. The method of claim 1, wherein reading the information in the RFID unit includes reading the information from a plurality of RFID units for a plurality of assemblies in a production area.

6. The method of claim 5, wherein reading the information from a plurality of RFID units includes reading the information from a plurality of RFID units using anti-collision technology.

7. The method of claim 1, wherein collecting information associated with manufacture of an implantable medical device includes reading the information with a bar code reader and storing the information in a computer.

8. The method of claim 1, wherein storing the information into an RFID unit includes transferring the information from a computer to the RFID unit using the RF communication device controlled by the computer.

9. The method of claim 1, further comprising packaging the RFID unit with a finished assembly of the implantable medical device.

10. The method of claim 9, wherein packaging the RFID unit with the finished assembly includes packaging the RFID unit with an implantable electrical lead.

11. The method of claim 9, wherein packaging the RFID unit with the finished assembly includes packaging the RFID unit with an implantable pulse generator.

12. A method comprising:
    collecting information related to manufacture of a first device, wherein the first device is an implantable medical device;
    storing the information in a second device, wherein the second device includes an RF communication device;
    storing the information into a plurality of third devices, wherein the third devices are passive RFID units, each passive RFID unit associated with a subassembly of the implantable medical device; and
    updating the information stored in the passive RFID units during manufacturing of the implantable medical device.

13. The method of claim 12, wherein storing the information into the RFID units includes:
    reading information stored in the plurality of RFID units;
    combining the information; and storing the information into one RFID unit for a finished assembly.

14. A method comprising:
collecting information related to manufacture of a first device, wherein the first device is an implantable medical device;
storing the information in a second device, wherein the second device includes an RF communication device;
storing the information in a third device, wherein the third device is a passive RFID unit;
reading and updating the information stored in the passive RFID unit as manufacturing of the implantable medical device progresses; and
providing readable information stored in the passive RFID unit during an implant procedure for the implantable medical device.

15. The method of claim 14, wherein providing readable information includes:
reading information with an external programmer; and
providing information for storage into the implantable medical device during an implant procedure, and wherein the implantable medical device is operable to alter its settings based on the provided information.

16. The method of claim 15, wherein the method further includes providing storage for entering information concerning the implant procedure into the RFID unit.

17. The method of claim 16, wherein providing storage includes providing storage for entering patient information into the RFID unit.

18. The method of claim 16, wherein the method further includes reading implant procedure information from an RFID unit returned to a manufacturer.

19. A system comprising:
a first device, wherein the first device is an implantable medical device; and
at least one second device, wherein the second device is an a passive RFID unit external to the implantable medical device, the passive RFID unit packageable with the implantable medical device, and wherein the passive RFID unit is to contain stored information, including data related to manufacturing of the implantable medical device, and further wherein the information is to be stored using a third device that includes an RF communication device.

20. The system of claim 19, wherein the RFID unit includes:
a transceiver circuit;
a radio frequency (RF) antenna coupled to the transceiver circuit;
memory; and
a controller circuit coupled to the memory and the transceiver circuit, the controller circuit operable to control memory access and to control transfers of information using the transceiver circuit.

21. The system of claim 20, wherein the RFID unit further includes a power circuit coupled to the transceiver circuit, memory and controller circuit, wherein the power circuit converts energy received during RF communications into power for the RFID unit.

22. The system of claim 19, wherein the at least one RFID unit includes a plurality of RFID units, wherein the plurality includes RFID units able to communicate over different distance ranges.

23. The system of claim 22, wherein the plurality of RFID units include a first passive RFID unit configured to transfer data to the RF communication device over short distances, a second passive RFID unit configured to transfer data to the RF communication device over medium distances, and a third passive RFID unit configured to transfer data to the RF communication device over long distances.

24. The system of claim 19, wherein a package for the implantable medical device includes external packaging and internal sterile packaging, and wherein the RFID unit is to be packaged within the internal sterile packaging.

25. The system of claim 19, wherein the system further includes the RF communication device operable to read data from, and write data to, the RFID unit.

26. The system of claim 25, wherein the communication device is operable to write patient data into the RFID unit.

27. The system of claim 25, wherein the implantable medical device includes an electrical lead, and wherein the stored information includes a lead impedance of the electrical lead.

28. The system of claim 25, wherein the communication device is operable to transfer data read from the RFID unit into the implantable medical device.

29. The system of claim 28, wherein the communication device is operable to write setting information for the implantable medical device into the RFID unit.

30. The system of claim 25, wherein the communication device is operable to communicate with the implantable medical device, and wherein the implantable medical device is operable to adopt a set of operating parameters reduced from a set of possible operating parameters based at least in part on the data transferred from the RFID unit.

31. The system of claim 30, wherein the implantable medical device includes a cardioverter defibrillator.

32. The system of claim 25, wherein the communication device is operable to communicate with a computer network.

33. The system of claim 32, wherein the communication device is operable to compare data read from the RFID unit to recall data provided on the computer network.

34. A method comprising:
packaging a first device, wherein the first device is an implantable medical device;
packaging a second device with the implantable medical device and external to the implantable medical device, wherein the second device is a passive RFID unit; and
providing readable information related to manufacturing of the implantable medical device in the passive RFID unit by storing the information using a third device, wherein the third device includes an RF communication device.

35. The method of claim 34, wherein the method further includes providing for storage of patient data into the RFID unit.

36. The method of claim 34, wherein the method further includes providing for storage of physician data into the RFID unit.

37. The method of claim 34, wherein the implantable medical device includes at least one medical device selected from the group consisting of:
an implantable pulse generator;
an implantable lead;
a guide wire; and
a catheter.

* * * * *